United States Patent [19]

Lund

[11] 4,241,181

[45] Dec. 23, 1980

[54] BROTH MEDIUM FOR DETECTION OF DNASE-POSITIVE MICROORGANISMS

[75] Inventor: Marlys E. Lund, Eden Prairie, Minn.

[73] Assignee: Minnesota Mining and Manufacturing Company, Saint Paul, Minn.

[21] Appl. No.: 35,290

[22] Filed: May 2, 1979

[51] Int. Cl.$^3$ .............................................. C12Q 1/04
[52] U.S. Cl. ..................................... 435/34; 435/36; 435/38; 435/253; 435/254; 435/255
[58] Field of Search ............... 435/253, 254, 255, 256, 435/243, 29, 34, 36, 38, 35, 37

[56] References Cited

U.S. PATENT DOCUMENTS 4,035,238  7/1977  Meyer et al. ........................... 435/36

OTHER PUBLICATIONS

Jeffries et al., "Rapid Method for Determining the Activity of Microorganisms on Nucleic Acids," Journal of Bacteriology, vol. 73, p. 591, 1957.
R. V. F. Lachica et al., "Convenient Assay of Staphylococcal Nuclease by the Metachromatic Well-Agar Diffusion Technique," Applied Microbiology, vol. 24, No. 6, pp. 920–923; 1972.
Blazevic and Ederer, Principles of Biochemical Tests in Diagnostic Microbiology, John Witz and Sons, pp. 37–39, 1975.
R. V. F. Lachica et al., "Metachromatic Agar–Diffusion Methods for Detecting Staphylococcal Nuclease Activity", Applied Microbiology, vol. 21, No. 4, pp. 585–587, 1971.
Janice Schreier, "Modification of Deoxyribonuclease Test Medium for Rapid Identification of Serratin Marcescens", The American Journal of Clinical Pathology, vol. 51, No. 6, pp. 711–716, 1969.

*Primary Examiner*—Robert J. Warden
*Attorney, Agent, or Firm*—Cruzan Alexander; Donald M. Sell; Carolyn A. Bates

[57] ABSTRACT

A broth medium for the detection of DNAse-positive microorganisms. The medium contains conventional nutrients for growing the microorganisms, a source of essential divalent cations to insure activity of the DNAse and a biological indicator comprising DNA, toluidine blue and lambda carrageenan in sufficient quantity so that the medium turns from blue to a visually distinguishable reddish-pink or reddish-violet color in the presence of DNAse-positive microorganisms.

11 Claims, No Drawings

BROTH MEDIUM FOR DETECTION OF DNASE-POSITIVE MICROORGANISMS

This invention relates to a broth medium containing an indicator substance which undergoes a color change in the presence of the enzyme DNAse. More specifically, the broth contains the dye toluidine blue as the indicator substance. A further aspect of the invention relates to broth medium which can be dried in microquantities for storage and handling and later reconstituted by the addition of water.

The ability of an organism to break down deoxyribonucleic acid (DNA) by means of a deoxyribonuclease has been used clinically to differentiate and identify groups of microorganisms. DNAse is an extracellular enzyme that hydrolyzes DNA to yield oligonucleotides (chains of several deoxyribonucleotides). The DNAse of *Serratia marcescens* yields di, tri-, and tetranucleotides. The DNAse of Group A streptococci produces predominately products having a chain length of 3 to 10 deoxyribonucleotide units, but also produces mononucleotides.

The physical and chemical properties of DNA are different from those of oligonucleotides or mononucleotides and these differences are utilized to detect the hydrolysis of DNA by DNAse—and thereby the presence of DNAse-positive microorganisms.

Several methods are described in the prior art for detecting hydrolysis of DNA by DNAse, all of which suffer from one or more disadvantages in clinical use.

The first such method was described by Jeffries et al, "Rapid Method for Determining the Activity of Microorganisms on Nucleic Acids", J. Bacteriol. 73:590 (1957). This method is based on the fact that DNA is precipitated by acid, whereas the oligonucleotides liberated by hydrolysis are soluble in acid. After incubation of the microorganisms on agar plates containing DNA, acid is added. If DNAse negative organisms are present the unhydrolysed DNA will precipitate causing the medium around the organisms to become cloudy. Conversely, if DNAse-positive organisms are present, a clear zone will form around the organisms. When this test is carried out in a liquid or broth medium, the procedure becomes more complicated and time-consuming. Because of the turbidity of the culture cells themselves, the cells must first be separated from the broth by centrifugation. Since the DNAse is released into the medium during incubation, the acid is then added to the supernatant.

Several clinical methods have been developed in which DNAse test medium is modified by the addition of an indicator dye. Lachica et al, "Convenient Assay for Staphylococcal Nuclease by the Methachromic Well-Agar-Diffusion Technique", *Appl. Microbiol* 24:920–923, 1972, describe a DNAse test medium in which the dye toluidine blue is added to detect DNA hydrolysis. When toluidine blue is complexed with DNA it stains blue, but when DNA is hydrolyzed to oligonucleotides or mononucleotides by DNAse, the color changes to pink in the presence of agar. The disadvantage of known DNAse test media containing toluidine blue is that they contain agar and therefore cannot exist as a liquid or broth medium at room temperature. They cannot be feasibly dried for storage and handling and then reconstituted to a broth.

DNAse test media have been modified by the addition of a methyl green indicator. Methyl green combines with DNA to form a greem complex. If DNA is hydrolyzed, the methyl green is released and becomes a colorless compound. A modification of this type of medium is described in U.S. Pat. No. 4,035,238 to Meyer et al. According to the method of Meyer et al, "The DNA methyl green is changed to reddish purple by sequentially adding to a solution containing it supplement VX from Difco and Vitamin $B_{12}$." When the red vitamin $B_{12}$ is added, the medium turns reddish purple. When a microorganism is added which produces DNAse, the reddish purple color changes to bluish purple. Potassium tellurite and amphoterricin B are also present in the medium to inhibit gram-negative organisms and yeast, respectively.

Media utilizing methyl green as the indicator material are desirable in one respect because they can exist as broths. However, methyl green methods involve an extremely subtle color change which is difficult to read visually, particularly in a broth medium.

The DNAse test medium of the present invention successfully overcomes the disadvantages associated with prior art media incorporating indicator dyes. The medium of the present invention is a broth medium capable of being easily dehydrated for storage and handling, (in, for example, nutrient wells of a plastic tray) and later reconstituted prior to use. Furthermore, the medium provides a clear and unambiguous rapid color change in the presence of DNAse-positive microorganisms.

According to the invention there is provided a broth medium for the detection of DNAse-positive microorganisms comprising: (a) an aqueous solution containing conventional essential nutrients; (b) a source of divalent cations; and (c) a biological indicator comprising toluidine blue O, lambda carrageenan and DNA is sufficient quantity so that said medium turns to a visually distinguishable reddish-pink to reddish-violet color in the presence of DNAse-positive microorganisms.

The primary novel feature of the invention resides in the combination of the lambda carrageenan and DNA in a broth medium. The medium may be easily dried in micro quantities and successfully reconstituted at room temperature by the addition of water prior to inoculation with the test microorganisms. The medium is ideal for use in microbial test trays containing a plurality of nutrient wells for microorganism identification.

Among essential ingredients of the broth are conventional nutrients for growing the microorganisms. Generally, these nutrients are provided by a carbon source and a nitrogen source. In the preferred embodiment of the invention set forth in Example 1 below, the carbon is provided by glucose and the nitrogen is provided by peptone. However, any commonly utilized carbohydrate or organic acid may be used to supply the carbon. Likewise, the nitrogen source may be any of those readily available in commerce.

Also required is a source of the essential divalent cations $Ca^{++}$ and $Mg^{++}$ which are believed to be required for bacterial DNAse activity. Since all of the ingredients must be water-soluble, source of these divalent cations are generally water-soluble salts magnesium and calcium. In the preferred embodiment of the invention, $CaCl_2$ and $MgSO_4$ are added for this purpose.

The biological indicator is a combination of the dye toluidine blue, lambda carrageenan and DNA. Toluidine blue is a metachromatic dye. Metachromasia is the property whereby a dye will not stain true because of complexes formed with some substances which result in an absorption spectrum different from the original dye. The true, or orthochromatic, staining of toluidine blue is blue, whereas metachromatic staining results in a pink to red to violet color. When toluidine blue is complexed with DNA it stains blue, but when complexed with lambda carrageenan (acid polysaccharide derived from seaweed) metachromasia occurs and the dye stains reddish-pink to reddish-violet. Although it was previously known that toluidine blue exhibits metachromatic staining with acid polysaccharides, (Michaelis and Granick, "Metachromasy of Basic Dye Stuffs", J. Amer. Chem. Society, Vol. 67, July, 1945, p. 1212–1219), it was not known that with the combination of toluidine blue, carrageenan and DNA, toluidine blue has greater affinity for the DNA than for the carrageenan. The DNA thus stabilizes the toluidine blue in its orthochromic state of blue. However, when a DNAse producing microorganism is present, the DNA is hydrolysed, leaving the toluidine blue unprotected from the carrageenan and the dye changes to its reddish-pink or reddish-purple metachromic form. A color change from blue to reddish-pink or reddish-purple observed with the broth of the invention is a positive identification of the presence of DNAse producing microorganisms.

The concentration of the ingredients forming the biological indicator portion of the broth is somewhat critical to the achievement of a readily identifiable color change. It has been found for optimum readability the toluidine blue should be present in an amount ranging from 0.002 to 0.005 percent by weight of the broth, lambda carrageenan in an amount ranging from 0.003 to 0.2 percent by weight of the broth, and DNA in an amount ranging from 0.02 to 0.035 percent by weight of the broth.

Since all ingredients of the broth must be water-soluble and non-gelling at room temperature, lambda carrageenan was selected over other carrageenans for its non-gelling properties. Carrageenan also exhibits the desirable property of resisting attack by bacterial enzymes. This feature minimizes false negative results.

The pH of the broth is preferably between 5.5 and 8.5. A buffer such as $K_2HPO_4$ may optionally be included in the broth to insure the proper pH. Other optional ingredients include a concentrated yeast nitrogen base to supply trace minerals and vitamins for enzyme activity.

An important aspect of the broth of the invention is its capability to be dried and stored in microquantities in wells of disposable test trays without deterioration for up to six months and then be quickly and easily reconstituted with distilled water prior to inoculation with microorganisms.

The following Example 1 provides a preferred, but not limiting, embodiment of the broth medium of the invention.

EXAMPLE 1

Combine in a flask:

| | |
|---|---|
| Glucose | 0.4 g |
| Peptone (from Difco) | 0.8 g |
| Beef extract (from Difco) | 0.4 g |
| $K_2HPO_4$ | 1.0 g |
| Lambda carrageenan (from Sigma) | 0.04 g |
| DNA (from Difco) | 0.09 g |
| Distilled water | 100 ml |

The solution is brought to a rolling boil with continuous stirring to completely dissolve the ingredients. (Caution: the solution boils over very readily). After all components are completely dissolved, 0.6 ml of 2% toluidine blue 0 is slowly added while stirring vigorously. When completely mixed, the solution is covered and autoclaved at 121° C. for 15 minutes, with the magnetic stir bar left in the flask. After removing from the autoclave, the solution is placed on a cool (room temperature) magnetic stir plate and stirred vigorously as the preparation cools. When cooled to room temperature the following ingredients are aseptically added:

| | | | |
|---|---|---|---|
| 30% $MgSO_4 \cdot 7H_2O$ | | 1.0 ml | |
| 30% $CaCl_2 \cdot 2H_2O$ | | 0.2 ml | |
| 10X yeast nitrogen base* | | 1.0 ml | |
| Ammonium sulfate | 5 g | Boric acid | 500 µg |
| L-histidine monohydrochloride | 10 mg | Copper suflate | 40 µg |
| dl-methionine | 20 mg | Potassium iodide | 100 µg |
| dl-tryphophane | 20 mg | Ferric chloride | 200 µg |
| Biotin | 2 µg | Manganese sulfate | 400 µg |
| Calcium pantothenate | 400 µg | Sodium molybdate | 200 µg |
| Folic acid | 2 µz | Zinc sulfate | 400 µg |
| Inositol | 2000 µg | | |
| Niacin | 400 µg | $KH_2PO_4$ | 1 g |
| p-aminobenzoic acid | 200 µg | Magnesium sulfate | 0.5 g |
| pyridoxine hydrochloride | 400 µg | Sodium chloride | 0.1 g |
| riboflavin | 200 µg | Calcium chloride | 0.1 g |
| thiamine hydrochloride | 400 µg | | |

*Contains per liter of single strength yeast nitrogen base.

The solution is mixed well and decanted into sterile centrifuge tubes and centrifuged to settle the precipitate. The sterile supernate is aseptically decanted into a sterile flask, discarding the precipitate.

This formulation is four times the concentration of the medium which is actually used in microorganism identification tests. If the broth is to be used immediately, it should be diluted 1 to 4 with distilled water.

The above concentration medium works well if the broth is to be dried and stored. Generally, when the broth is placed in the shallow wells of a test tray, about 25 microliters of the above concentrated broth is dispensed into the well. The broth is allowed to air dry (or dried by other conventional means such as vacuum drying, forced hot air drying or lyophilization). Each well is then reconstituted by the addition of 100 microliters of sterile distilled water prior to inoculation.

Following inoculation, the organisms are allowed to incubate for about 16 to 18 hours at 35° C. The broth is then examined visually. If the original blue color is present, it may be deduced that the organism with which the broth was inoculated is a type which does not produce DNAse. However, if the broth has changed to a reddish-pink or reddish-violet color, it may be concluded that a DNAse positive organism is present.

What is claimed is:

1. A broth medium for the detection of DNAse-positive microorganisms comprising:
    (a) a source of conventional nutrients to support growth of said microorganisms;
    (b) a source of essential divalent cations in sufficient concentration to insure activity of said DNAse; and
    (c) a biological indicator comprising DNA, toluidine blue and lambda carrageenan in sufficient quantity so that said medium turns to a visually distinguishable reddish-pink or reddish-violet color in the presence of DNAse-positive microorganisms.

2. The medium according to claim 1 wherein said DNA is present in an amount ranging from about 0.02 to 0.035 percent by weight of said medium, said toluidine blue is present in an amount ranging from about 0.002 to 0.005 percent by weight of said medium and said lambda carrageenan is present in an amount ranging from about 0.003 to 0.2 percent by weight of said medium.

3. The medium according to claim 1 wherein said source of conventional nutrients comprises a carbon source and a nitrogen source.

4. The medium according to claim 1 wherein said carbon source is glucose.

5. The medium according to claim 1 wherein said nitrogen source is peptone.

6. The medium according to claim 1 wherein said divalent cations are provided by magnesium and calcium salts.

7. The medium according to claim 1 further comprising a buffer to maintain the pH of said medium between 5.5 and 8.5.

8. The medium according to claim 7 wherein said buffer is $K_2HPO_4$.

9. The medium according to claim 1 further comprising yeast nitrogen base.

10. The medium according to claim 1 in a dehydrated state which may be reconstituted by the addition of water.

11. A broth medium for DNAse-positive microorganisms comprising about:

0.1 gram glucose
0.2 gram peptone
0.1 gram beef extract
0.25 gram $K_2HPO_4$
0.01 gram lambda carrageenan
0.0225 gram DNA
0.15 ml 2% (W/V) toluidine blue 0
0.25 ml 30% (W/V) $MgSO_4.7H_2O$
0.05 ml 30% (W/V) $CaCl_2.2H_2O$
0.25 ml 10X yeast nitrogen base
100 ml Distilled water.

* * * * *